United States Patent
Oyama

(10) Patent No.: US 11,647,892 B2
(45) Date of Patent: May 16, 2023

(54) DISTAL END PORTION OF ENDOSCOPE, ENDOSCOPE INSERTION PORTION, AND ENDOSCOPE

(71) Applicant: OLYMPUS CORPORATION, Tokyo (JP)

(72) Inventor: Katsumi Oyama, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 340 days.

(21) Appl. No.: 17/147,575

(22) Filed: Jan. 13, 2021

(65) Prior Publication Data

US 2021/0127953 A1  May 6, 2021

Related U.S. Application Data

(63) Continuation of application No. PCT/JP2018/032872, filed on Sep. 5, 2018.

(51) Int. Cl.
*A61B 1/05* (2006.01)
*A61B 1/06* (2006.01)
(Continued)

(52) U.S. Cl.
CPC .......... *A61B 1/00096* (2013.01); *A61B 1/051* (2013.01); *A61B 1/0676* (2013.01);
(Continued)

(58) Field of Classification Search
None
See application file for complete search history.

(56) References Cited

U.S. PATENT DOCUMENTS 11,249,300 B1 * 2/2022 Lin .................. H04N 23/56
11,311,184 B2 * 4/2022 Sørensen ............... A61B 1/051
(Continued)

FOREIGN PATENT DOCUMENTS

JP    2005-80713 A    3/2005
JP    2007-075261 A   3/2007
(Continued)

OTHER PUBLICATIONS

International Search Report dated Nov. 27, 2018 issued in PCT/JP2018/032872.

*Primary Examiner* — John P Leubecker
(74) *Attorney, Agent, or Firm* — Scully, Scott, Murphy & Presser, P.C.

(57) ABSTRACT

A distal end portion of an endoscope includes: a flexible printed circuit board on which a light-receiving unit mounting section, a first extending section, a light-emitting unit mounting section, and a second extending section are formed continuously; a stand on which the light-receiving unit mounting section is disposed in contact with the stand; a protruding portion including an inner wall surface, a protruding end surface, and an outer wall surface, in which the first extending section is disposed in contact with the inner wall surface, the light-emitting unit mounting section is disposed in contact with the protruding end surface, and the second extending section is disposed in contact with the outer wall surface; and a distal end cover that covers the stand and the protruding portion, with the second extending section being sandwiched between the distal end cover and the protruding portion.

9 Claims, 19 Drawing Sheets

(51) Int. Cl.
*H04N 23/54* (2023.01)
*A61B 1/00* (2006.01)
*H04N 23/50* (2023.01)

(52) U.S. Cl.
CPC ........... *A61B 1/0684* (2013.01); *A61B 1/0011* (2013.01); *A61B 1/05* (2013.01); *H04N 23/54* (2023.01); *H04N 23/555* (2023.01)

(56) References Cited

U.S. PATENT DOCUMENTS

| | | |
|---|---|---|
| 11,382,490 B2 * | 7/2022 | Sørensen ........... A61B 1/00101 |
| 2004/0132491 A1 * | 7/2004 | Kim ....................... H04N 23/56 |
| | | 348/E5.025 |
| 2005/0124858 A1 | 6/2005 | Matsuzawa et al. |
| 2011/0118549 A1 | 5/2011 | Han |
| 2013/0035546 A1 | 2/2013 | Lin |
| 2013/0271588 A1 | 10/2013 | Kirma et al. |
| 2014/0210976 A1 | 7/2014 | Lin |
| 2019/0089875 A1 * | 3/2019 | Fan ........................ A61B 1/051 |

FOREIGN PATENT DOCUMENTS

| | | |
|---|---|---|
| JP | 2010-258582 A | 11/2010 |
| JP | 2012-195931 A | 10/2012 |
| JP | 2013-544617 A | 12/2013 |
| JP | 2014-14611 A | 1/2014 |
| JP | 2016-150214 A | 8/2016 |
| WO | WO 2012/077116 A1 | 6/2012 |

\* cited by examiner

DISTAL END PORTION OF ENDOSCOPE, ENDOSCOPE INSERTION PORTION, AND ENDOSCOPE

CROSS-REFERENCE TO RELATED APPLICATION

This application is a continuation application of PCT/JP2018/032872 filed on Sep. 5, 2018, the entire contents of which are incorporated herein by this reference.

BACKGROUND OF THE INVENTION

1. Field of the Invention

The present invention relates to a distal end portion of an endoscope, in which an image pickup device and a light-emitting element are disposed, an endoscope insertion portion, and an endoscope.

2. Description of the Related Art

Conventionally, endoscopes have been widely used in medical fields and industrial fields. With such an endoscope, an inside of a tubular path can be observed by inserting an elongated insertion portion of the endoscope into the tubular path. As an example of an endoscope to be used when displaying an image of a subject or an object on a monitor or the like, an endoscope is known, in which an image pickup device such as a CCD is disposed in a distal end portion of an insertion portion of the endoscope.

In such an endoscope, an image pickup device is generally mounted on a flexible printed circuit board (hereinafter, just referred to as FPC), and the FPC on which the image pickup device is mounted is bent in a desired shape, to be efficiently disposed in a distal end portion of an endoscope, a size reduction of which is required. Japanese Patent Application Laid-Open Publication No. 2010-258582, for example, discloses a configuration in which an FPC (circuit board) on which an image pickup device is mounted is disposed such that the FPC is bent so as to form a triangle shape behind the rear surface side of the image pickup device.

Incidentally, the endoscope of such a type may have a configuration in which a light source element such as an LED is disposed in a distal end portion, instead of a configuration in which a light guide is used to guide illumination light to the distal end portion. In this case, the light source element is disposed in the distal end portion, with the light source element being mounted on the same FPC on which the image pickup device is mounted, to thereby enable simplification of the configuration of the distal end portion.

SUMMARY OF THE INVENTION

A distal end portion of an endoscope according to one aspect of the present invention includes: a light-receiving unit having a first height; a light-emitting unit having a second height lower than the first height; a flexible printed circuit board on which a light-receiving unit mounting section, a first extending section, a light-emitting unit mounting section, and a second extending section are formed, the light-receiving unit mounting section including a first surface on which the light-receiving unit is mounted, the first extending section extending from the light-receiving unit mounting section, the light-emitting unit mounting section provided continuously to the first extending section and including a first surface on which the light-emitting unit is mounted, and a second extending section extending from the light-emitting unit mounting section; a stand including a seat surface on which a second surface of the light-receiving unit mounting section is disposed in contact with the seat surface, the second surface being a rear surface of the first surface of the light-receiving unit mounting section; a protruding portion protruded from the stand, with the protruding portion adjoining the seat surface, the protruding portion including an inner wall surface adjoining the seat surface, a protruding end surface, and an outer wall surface which is opposite side of the inner wall surface, in which a second surface as a rear surface of the first extending section is disposed in contact with the inner wall surface, a second surface as a rear surface of the light-emitting unit mounting section is disposed in contact with the protruding end surface, and a second surface as a rear surface of the second extending section is disposed in contact with the outer wall surface; and a cover member that covers the light-receiving unit, the light-emitting unit, the stand, and the protruding portion.

An endoscope insertion portion according to one aspect of the present invention includes the distal end portion of the endoscope.

An endoscope according to one aspect of the present invention includes the distal end portion of the endoscope.

DETAILED DESCRIPTION OF THE PREFERRED EMBODIMENTS

Figure 1:
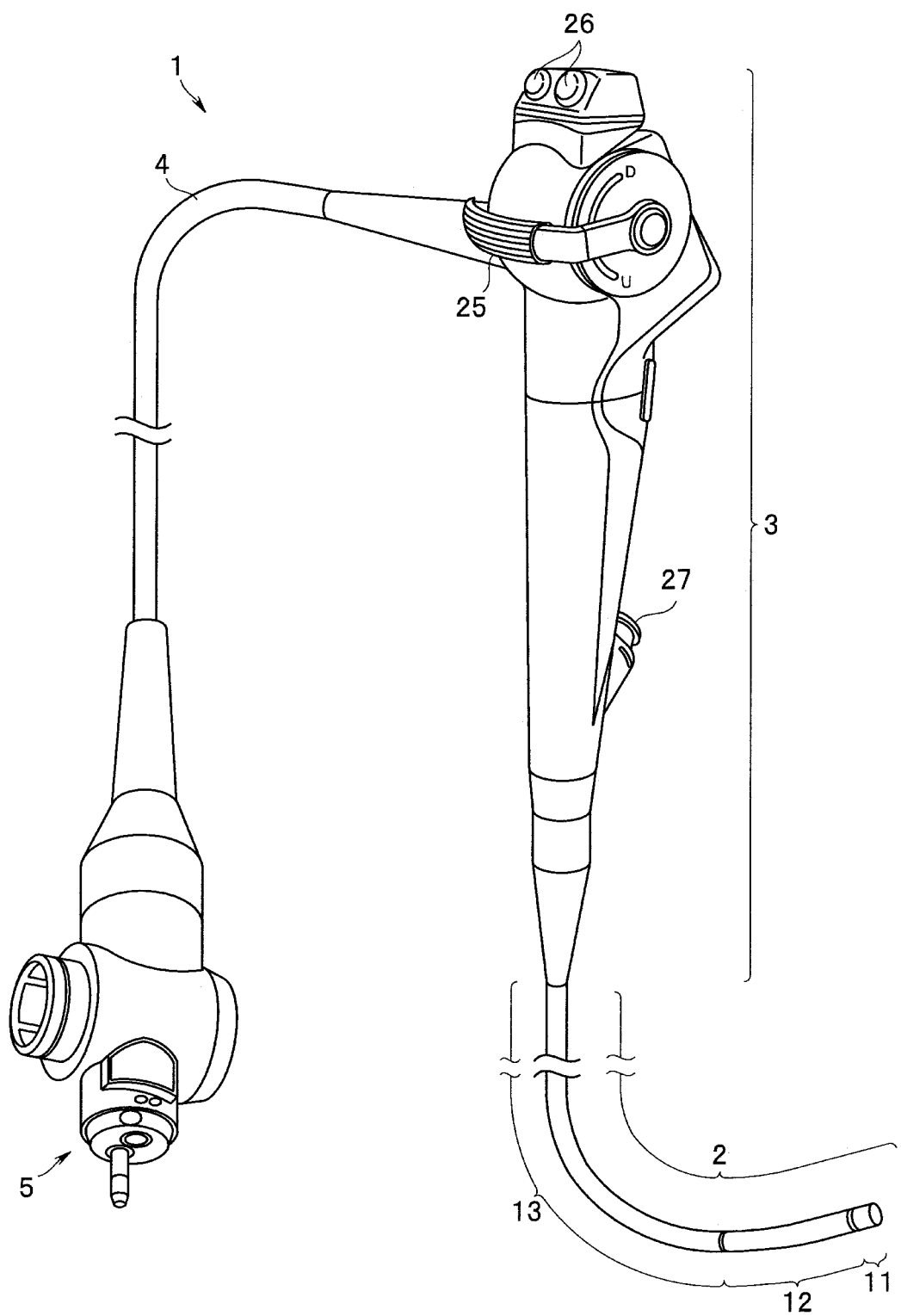
FIG. 1 is an appearance perspective view of an endoscope.
Figure 2:
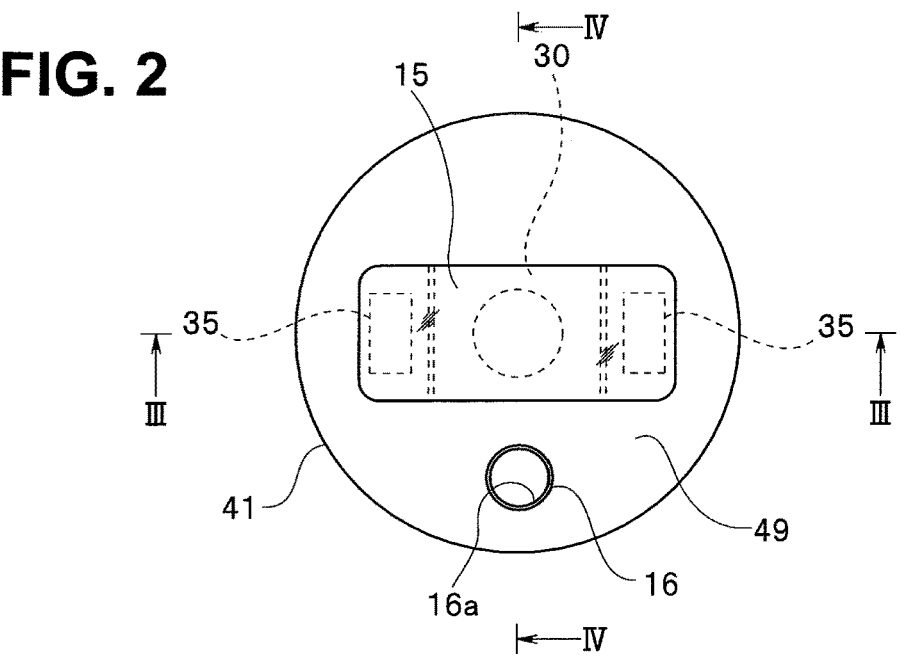
FIG. 2 is a view illustrating an end surface of a distal end portion.
Figure 3:
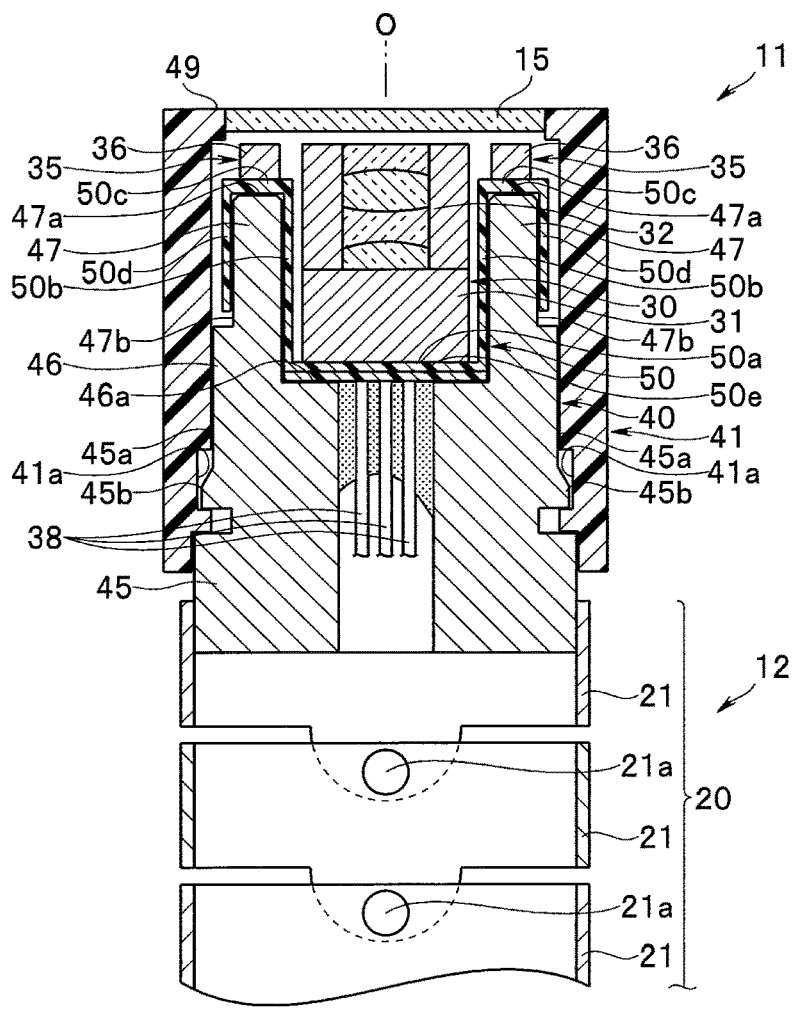
FIG. 3 is a sectional view taken along the line in FIG. 2.
Figure 4:
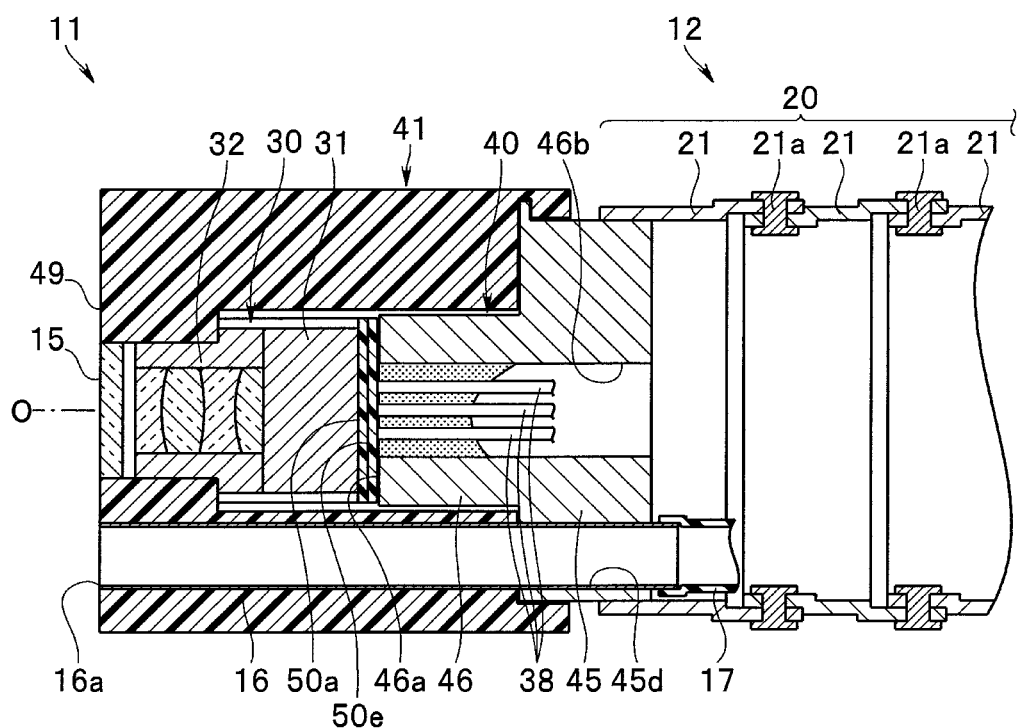
FIG. 4 is a sectional view taken along the line IV-IV in FIG. 2.
Figure 5:
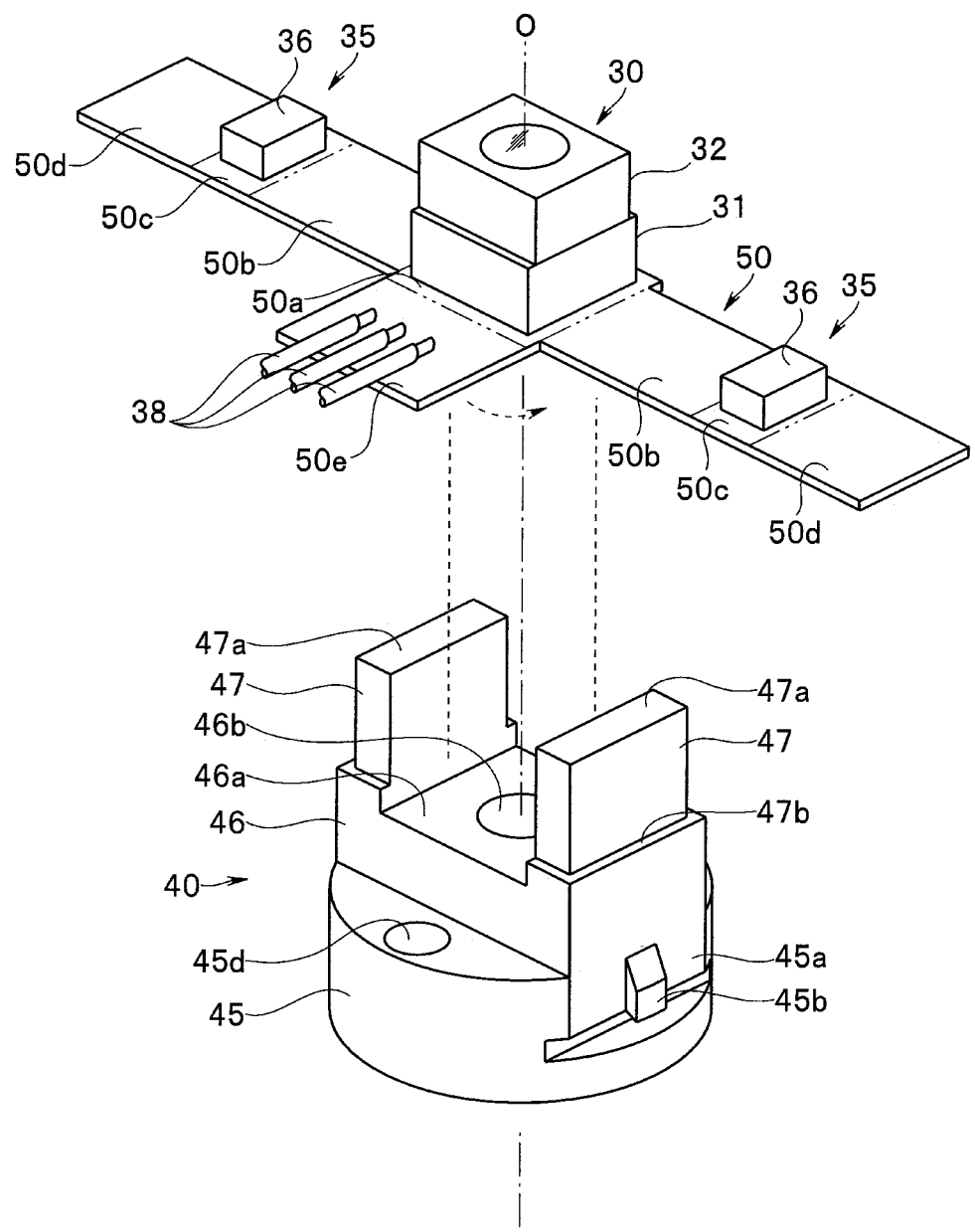
FIG. 5 is an exploded perspective view illustrating a flexible printed circuit board on which a light-receiving unit and a light-emitting unit are mounted, and a distal end constituting section.
Figure 6:
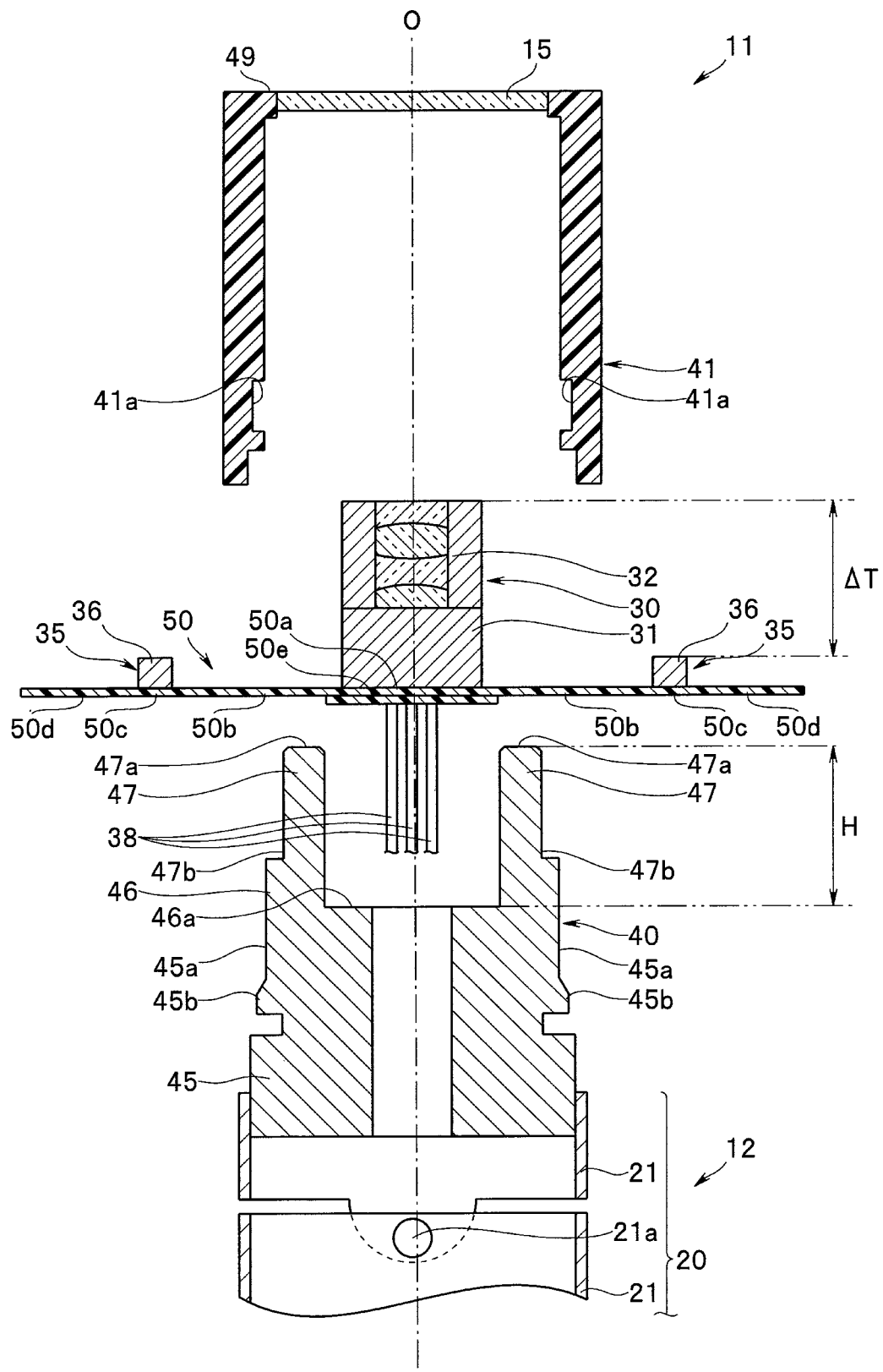
FIG. 6 is an explanatory view illustrating an assembly process of the distal end portion.
Figure 7:
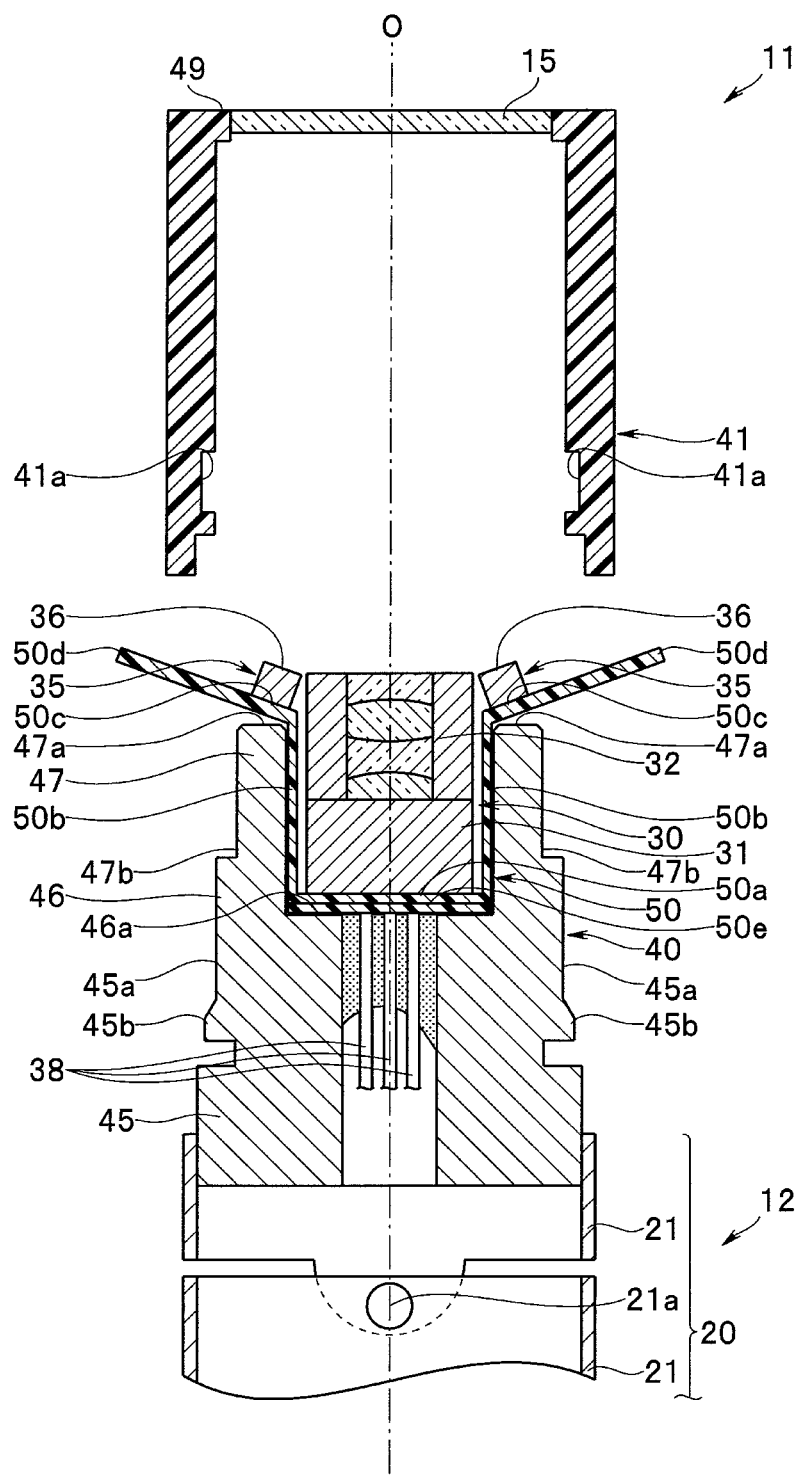
FIG. 7 is an explanatory view illustrating the assembly process of the distal end portion.
Figure 8:
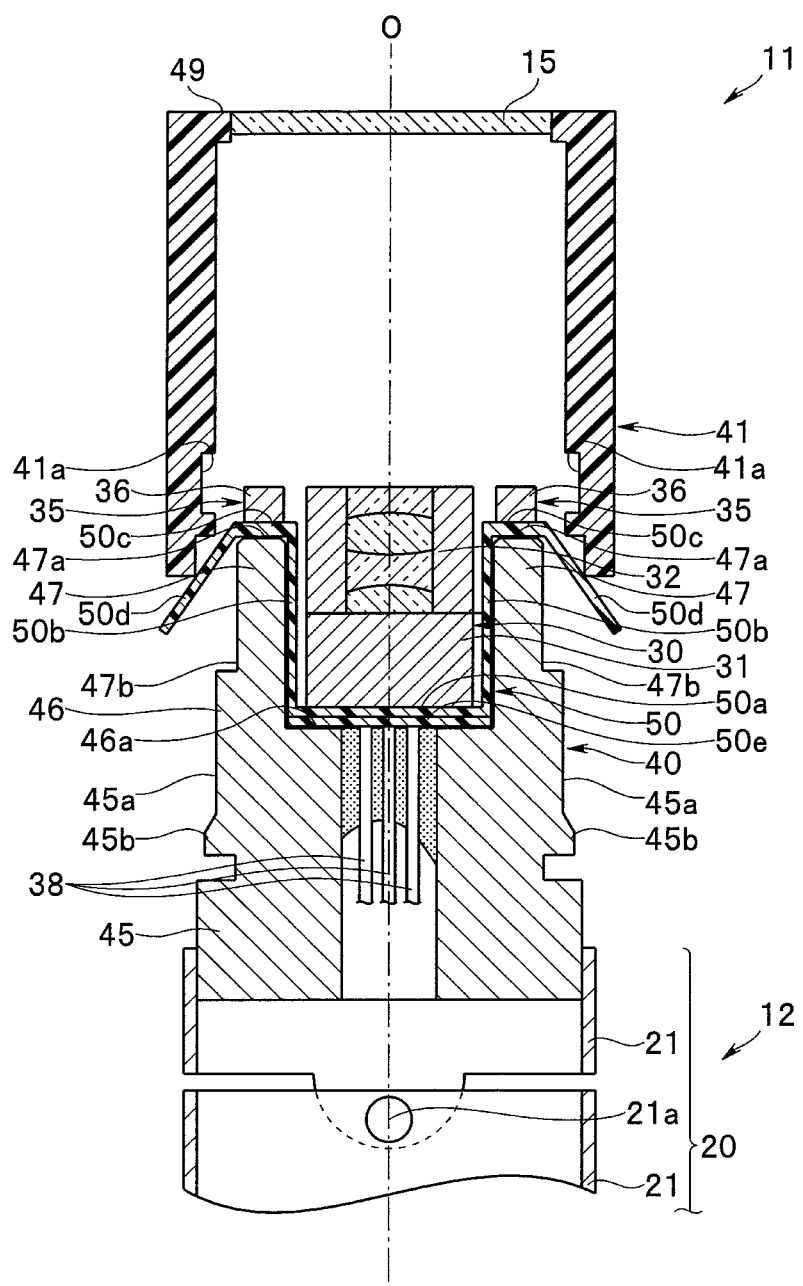
FIG. 8 is an explanatory view illustrating the assembly process of the distal end portion.

Hereinafter, an embodiment of the present invention will be described with reference to drawings. Figures relate to one embodiment of the present invention. FIG. 1 is an appearance perspective view of an endoscope, FIG. 2 is a view of an end surface of a distal end portion, FIG. 3 is a sectional view taken along the line in FIG. 2, FIG. 4 is a sectional view taken along the line IV-IV in FIG. 2, FIG. 5 is an exploded perspective view illustrating a flexible printed circuit board on which a light-receiving unit and a light-emitting unit are mounted, and a distal end constituting section, and FIGS. 6 to 8 are explanatory views each illustrating an assembly process of the distal end portion.

An endoscope 1 illustrated in FIG. 1 is an endoscope for urinary organs such as a renal pelvis (pyeloureteroscope), for example. The endoscope 1 includes an insertion portion 2 having an elongated shape and configured to be inserted into a body cavity of a subject, an operation portion 3 provided at a proximal end of the insertion portion 2, and a universal cable 4 extended from a proximal end of the operation portion 3.

As illustrated in FIG. 1, the insertion portion 2 includes a distal end portion 11, a bending portion 12, and a flexible tube portion 13. The distal end portion 11 is located on a distal end side of the insertion portion 2, the bending portion 12 is disposed continuously to a proximal end of the distal end portion 11, and the flexible tube portion 13 has a flexibility and is disposed continuously to a proximal end of the bending portion 12.

The distal end portion 11 includes inside thereof a light-receiving unit 30 and a pair of light-emitting units 35, for example. The light-receiving unit 30 includes an image pickup device 31 such as a CCD, a CMOS, or the like. Each of the pair of the light-emitting units 35 includes a light source element 36 such as a light-emitting diode (LED), or the like (see FIGS. 2 to 5).

The light-receiving unit 30 of the present embodiment includes the image pickup device 31 and an objective optical system 32, for example. The objective optical system 32 includes a stack of a plurality of objective lenses (stacked lenses) disposed on a light-receiving surface side of the image pickup device 31. On the other hand, each of the light-emitting units 35 of the present embodiment is configured by the light source element 36 as a single entity, for example.

Note that a pair of (two) light-emitting units 35 are provided in the distal end portion 11 in the present embodiment. However, one light-emitting unit 35 may be provided, for example.

Furthermore, the distal end portion 11 holds, inside thereof, a channel connecting tube 16 (see FIG. 4). A distal end of the channel connecting tube 16 is disposed on a surface which is the same as a distal end surface of the distal end portion 11, thereby forming a channel opening portion 16a on the distal end portion 11 (see FIGS. 2 and 4). A proximal end side of the channel connecting tube 16 is connected with a distal end side of a treatment instrument channel 17 inserted in the insertion portion 2.

The bending portion 12 includes a bending piece set 20 in which a plurality of bending pieces 21 are disposed continuously along an insertion axis direction. The respective bending pieces 21, which constitute the bending piece set 20, are coupled to each other so as to be swingable with respect to each other in up and down directions through a rotation shaft 21a, for example. With such a configuration, the bending portion 12 is bendable in two directions, i.e., the up and down directions, in conjunction with a rotation operation of a bending lever 25 provided on the proximal end side of the operation portion 3.

In the present embodiment, the up and down directions and the left and right directions of each component of the endoscope 1 are defined so as to coincide with the up and down directions and the left and right directions on an image picked up by the image pickup device 31. Note that the bending direction of the bending portion 12 is not limited to the two directions, i.e., the up and down directions, but may be two directions, i.e., the left and right directions, or four directions, i.e., the up, down, left, and right directions.

The operation portion 3 includes, on the proximal end side thereof, various types of switches 26 for the endoscope are provided, in addition to the above-described bending lever 25.

In addition, the operation portion 3 includes, on the distal end side thereof, a pipe sleeve 27 communicating with a proximal end side of the treatment instrument channel 17.

With such a configuration, the endoscope 1 of the present embodiment allows various types of treatment instruments such as a laser probe to be inserted into the treatment instrument channel 17 through the pipe sleeve 27. The treatment instrument or the like inserted into the treatment instrument channel 17 is guided to the distal end side of the insertion portion 2, to be protruded into the subject from the channel opening portion 16a of the distal end portion 11, thereby being capable of performing various kinds of treatment.

In addition, a liquid feeding apparatus can be connected to the pipe sleeve 27 through an adapter, not illustrated, etc. Such a configuration, for example, allows a fluid such as normal saline to flow through the treatment instrument channel 17 and to be discharged from the channel opening portion 16a.

In the present embodiment, in addition to the treatment instrument channel 17, various kinds of cables 38 (see FIG. 3), angle wires (not illustrated), and the like are inserted through the inside of the insertion portion 2 and the operation portion 3. The cables 38 are electrically connected to the light-receiving unit 30 and the light-emitting units 35. The angle wires are configured to bend the bending portion 12 in conjunction with the rotation operation of the bending lever 25.

Among the cables 38, the angle wires, and the like, the cables 38 are inserted into the universal cable 4 and connected to a video processor through a connector 5.

Next, specific description will be made on the configuration of the distal end portion 11 in the present embodiment.

As illustrated in FIGS. 3 to 5, the distal end portion 11 includes a distal end constituting section 40 made of a rigid material and a distal end cover 41 as a cover member covering the distal end constituting section 40.

The distal end constituting section 40 includes in the following order from the proximal end side thereof: a bending piece connecting section 45, a stand 46, and a pair of protruding portions 47. The stand 46 protrudes from the bending piece connecting section 45 in a direction of an optical axis O. The pair of protruding portions 47 protrude from the stand 46 in the direction of the optical axis O.

The bending piece connecting section 45 has a substantially columnar shape, for example, and a bending piece 21, which is located at the distal-most position in the bending piece set 20, is connected to the bending piece connecting section 45.

In addition, a pair of plane portions 45a are formed on the circumferential surface of the bending piece connecting section 45 at positions which are on the distal end side with respect to the part to which the bending piece 21 is connected. Each of the plane portions 45a includes an engaging claw 45b with which the distal end cover 41 is engaged.

Furthermore, the bending piece connecting section 45 includes a connecting tube insertion hole 45d through which the channel connecting tube 16 can be inserted along the direction of the optical axis O.

The stand 46 is formed, for example, in a substantially rectangular parallelepiped shape with a pair of side wall surfaces that are continuous respectively to the pair of plane portions 45a formed on the bending piece connecting section 45.

An end surface of the stand 46 is formed as a first seat surface 46a which is a seat surface on which the light-receiving unit 30 is disposed, and a cable insertion hole 46b communicating with the proximal end side of the bending piece connecting section 45 is open on the first seat surface 46a.

The protruding portions 47 are protruded from the stand 46 so as to adjoin the first seat surface 46a. More specifically, in the present embodiment, the respective protruding portions 47 are disposed at positions opposed to each other across the seat surface 46a. The protruding end surfaces of the protruding portions 47 are formed as second seat surfaces 47a on which the light-emitting units 35 are respectively disposed.

A height H of each of the protruding portions 47 (that is, the distance from the first seat surface 46a to each of the second seat surfaces 47a in the direction of the optical axis O) is set to be substantially equal to or slightly lower than a height difference $\Delta T$ between a height of the light-receiving unit 30 and a height of each of the light-emitting units 35. The height of the light-receiving unit 30 is defined as a first height, and the height of each of the light-emitting units 35 is defined as a second height.

In addition, stepped cutout portions 47b are formed respectively on the outer wall surfaces (that is, wall surfaces which are opposite side of the inner wall surfaces opposed to each other, with adjoining the first seat surface 46a) of the respective protruding portions 47, in order to form a predetermined gap between the distal end constituting section 40 and the distal end cover 41 to be described later.

Note that a pair of (two) protruding portions 47 are provided so as to correspond to the pair of (two) light-emitting units 35 in the present embodiment. However, if one light-emitting unit 35 is provided, for example, one protruding portion 47 is provided.

The distal end cover 41 is made of a resin member formed in a substantially cylindrical shape, the distal end of which is closed by a front wall portion 49.

The distal end cover 41 includes, at positions on the inner surface on the proximal end side thereof, recessed portions 41a which respectively engage with the engaging claws 45b.

In addition, on the front wall portion 49 of the distal end cover 41, a window portion 15 opposed to the first seat surface 46a and the second seat surfaces 47a is provided.

Between the distal end constituting section 40 and the distal end cover 41 thus configured, the light-receiving unit 30 and the light-emitting units 35 are held, with the light-receiving unit 30 and the light-emitting unit 35 being mounted on the one (same) flexible printed circuit board (FPC) 50.

On one surface of the FPC 50, a light-receiving unit mounting section 50a, a pair of first extending sections 50b, a pair of light-emitting unit mounting sections 50c, and a pair of second extending sections 50d are formed integrally. The light-receiving unit mounting section 50a includes a first surface on which the light-receiving unit 30 is mounted, the first surface being the one surface side of FPC 50. The pair of first extending sections 50b extend respectively to both sides from the light-receiving unit mounting section 50a. Each of the pair of light-emitting unit mounting sections 50c is formed continuously to each of the pair of first extending sections and includes a first surface on which the light-emitting unit 35 is mounted, the first surface being the one surface side of the FPC 50. The pair of second extending sections 50d extend respectively from the pair of light-emitting unit mounting sections 50c.

In the present embodiment, the length of each of the first extending sections 50b is set to a length substantially equal to the height H of each of the protruding portions 47. In addition, as illustrated in FIG. 5, for example, the first extending sections 50b, the light-emitting unit mounting sections 50c, and the second extending sections 50d according to the present embodiment are formed in the same width so as to have a shape of a series of band.

In the present embodiment, the pair of (two) first extending sections 50b, the pair of (two) light-emitting unit mounting sections 50c, and the pair of second extending sections 50d are provided so as to correspond to the pair of (two) light-emitting units 35. However, if one light-emitting unit 35 is provided, for example, one first extending section 50b, one light-emitting unit mounting section 50c, and one second extending section 50d are provided.

In addition, the FPC 50 includes a cable connecting section 50e which is formed integrally with the FPC 50. The cable connecting section 50e is provided continuously to the light-receiving unit mounting section 50a in a direction different from the directions in which the first extending sections 50b are respectively extended. The cable connecting section 50e includes terminal portions (not illustrated) configured to be electrically connected with the light-receiving unit 30 mounted on the light-receiving unit mounting section 50a and the respective light-emitting unit 35 mounted respectively on the light-emitting unit mounting sections 50c. The terminal portions are electrically connected respectively with the various types of cables 38.

Note that, in a case where terminal portions are formed by through holes or the like on a second surface which is opposite side of the first surface of the light-receiving unit mounting section 50a and the various cables 38 can be connected to the terminal portions, the cable connecting section 50e can be omitted from the FPC 50.

The FPC 50 on which the light-receiving unit 30 and the light-emitting units 35 are mounted is first brought into a bent state in which the second surface of the light-receiving unit mounting section 50a and the second surface of the cable connecting section 50e overlap with each other (see FIG. 6), and then the second surface side of the light-receiving unit mounting section 50a is fixed to the first seat surface 46a through the cable connecting section 50e (see FIG. 7).

In other words, an assembly worker or the like disposes the cable connecting section 50e on the first seat surface 46a while inserting the respective cables 38 into the cable insertion hole 46b, thereby causing the second surface side of the light-receiving unit mounting section 50a to be disposed in contact with the first seat surface 46a through the cable connecting section 50e.

Then, the cable insertion hole 46b is filled with an adhesive, and thereby the light-receiving unit mounting section 50a is fixed to the first seat surface 46a of the stand 46.

At this time, the respective first extending sections 50b extended from the light-receiving unit mounting section 50a are bent inwardly (light-receiving unit 30 side) by the inner wall surfaces, which adjoin the first seat surface 46a, of the respective protruding portions 47, and the second surfaces of the first extending sections 50b are disposed in contact respectively with the inner wall surfaces of the protruding portions 47.

After that, the distal end constituting section 40 is covered with the distal end cover 41, thereby causing the second surface sides of the light-emitting unit mounting sections 50c to be disposed in contact respectively with the second seat surfaces 47a (see FIG. 3).

In other words, when an assembly worker or the like mounts the distal end cover 41 on the distal end constituting section 40, the distal end cover 41 causes the second extending sections 50d of the FPC 50 to bend respectively toward the protruding portions 47 (see FIG. 8), and further covers the stand 46 and the protruding portions 47, with each of the second extending sections 50d sandwiched between the inner circumferential surface of the distal end cover 41 and each of the protruding portions 47.

This causes the second surface of each of the light-emitting unit mounting sections 50c to be disposed in contact with each of the second seat surfaces 47a formed respectively at the protruding ends of the respective protruding portions 47, and causes the second surface of each of the second extending sections 50d to be disposed in contact with each of the outer wall surfaces of the respective protruding portions 47.

More specifically, the length of each of the first extending sections 50b is set to the length substantially equal to the height H of each of the protruding portions 47. Therefore, when the respective second extending sections 50d are drawn toward the proximal end side of the distal end constituting section 40 by the distal end cover 41, the respective light-emitting unit mounting sections 50c are automatically positioned on the respective second seat surfaces 47a. At this time, each of the second extending sections 50d is held in a gap between each of the protruding portions 47 and the inner circumferential surface of the distal end cover 41, with the second surface of each of the second extending sections 50d being in contact with the outer wall surface of each of the protruding portions 47, which enables each of the light-emitting unit mounting sections 50c to be held on each of the second seat surfaces 47a without a need of a working such as adhesion.

With such configurations, the light-receiving unit 30 and the light-emitting units 35 are opposed to the window portion 15 formed on the distal end surface of the distal end portion 11, with the light-receiving unit 30 and the light-emitting units 35 being positioned such that the positions of the distal end surfaces in the direction of the optical axis O (the heights viewed from the proximal end side of the distal end portion 11) are substantially equal to each other.

According to such an embodiment, the distal end portion 11 is configured by one flexible printed circuit board 50, the stand 46, the protruding portions 47, and the distal end cover 41. The one flexible printed circuit board 50 includes: the light-receiving unit mounting section 50a including the first surface on which the light-receiving unit 30 is mounted; the first extending sections 50b extending from the light-receiving unit mounting section 50a; the light-emitting unit mounting sections 50c provided continuously to the respective first extending sections 50b, the light-emitting unit mounting sections 50c each having the first surface on which the light-emitting unit 35 is mounted; and the second extending sections 50d extending respectively from the light-emitting unit mounting sections 50c. The stand 46 includes the first seat surface 46a on which the second surface of the light-receiving unit mounting section 50a is disposed in contact with the first seat surface 46a. Each of the protruding portions 47 protrudes from the stand 46, with each of the protruding portions adjoining the first seat surface 46a, and includes the inner wall surface, and the protruding end surface (second seat surface 47a), and the outer wall surface, in which the second surface of each of the first extending sections 50b is disposed in contact with the inner wall surface, the second surface of each of the light-emitting unit mounting sections 50c is disposed in contact with the protruding end surface, and the second surface of each of the second extending sections 50d is disposed in contact with the outer wall surface. The distal end cover 41 includes the window portion 15 disposed so as to be opposed to the light-receiving unit 30 and the light-emitting unit 35, and covers the stand 46 and the protruding portions 47, with each of the second extending sections 50d sandwiched between the inner circumferential surface of the distal end cover and each of the protruding portions 47. Accordingly, it is possible to dispose the light-receiving unit and the light-emitting unit at appropriate positions with a simple configuration.

In other words, since the light-emitting units 35 are mounted on the one FPC 50 which is the same board on which the light-receiving unit 30 is mounted, there is no need for increasing the number of boards even when the light-emitting units 35 each including the light source element 36 are disposed in the distal end portion 11, which enables the simplification of the structure.

In such a configuration, the light-receiving unit 30 and the light-emitting units 35 that generally have different heights are mounted on the same FPC 50. Even in such a case, the protruding portions 47 that protrude from the stand 46 by a predetermined height are provided, and the light-emitting units 35 each having a height lower than the height of the light-receiving unit 30 are disposed on the second seat surfaces 47a formed at the protruding ends of the protruding portions 47, which enables the adjustment of the heights of the light-receiving unit 30 and the light-emitting units 35 to be performed easily.

In particular, the light-receiving unit 30 and the light-emitting units 35 are mounted on the same surface (on the first surface) of the FPC 50. Therefore, after the second surface of the light-receiving unit mounting section 50a is fixed to the first seat surface, the light-emitting units 35 can be disposed respectively on the second seat surfaces 47a with a simple work of bending the FPC 50 in substantially a crank shape.

Furthermore, since the work of bending the FPC 50 is performed in accordance with the shape of the protruding portions 47, with the light-receiving unit mounting section 50a as a starting point for bending, there is no need for performing a complicated positioning work and the like. Furthermore, when the distal end cover 41 is mounted on the distal end constituting section 40, each of the second extending sections 50d is sandwiched between the distal end cover 41 and each of the protruding portions 47. Such a configuration enables the light-emitting units 35 to be positioned at the appropriate positions without performing a work such as adhering of the light-emitting unit mounting sections 50c respectively to the second seat surfaces 47a in the extremely fine assembling process of the distal end portion 11.

Figure 9:
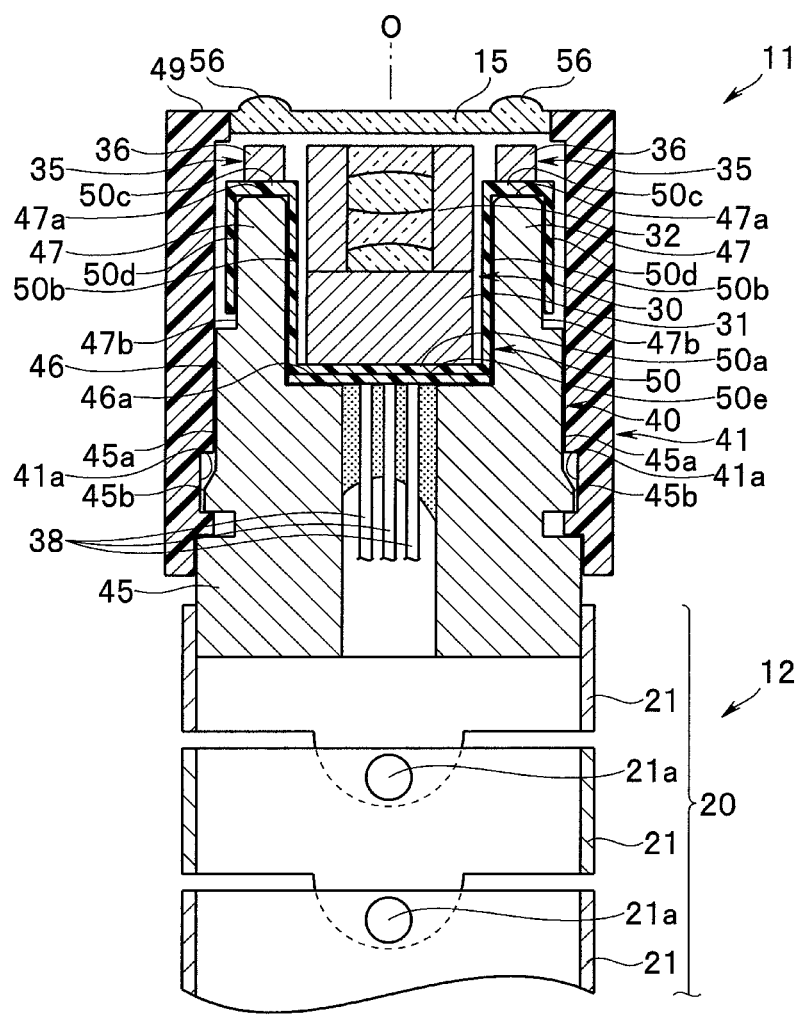
FIG. 9 relates to a first modification and is a sectional view of an essential part of a distal end portion.

In the above-described embodiment, as illustrated in FIG. 9, for example, illumination optical systems 56 opposed respectively to the light-emitting units 35 can be provided at the window portion 15.

Figure 10:
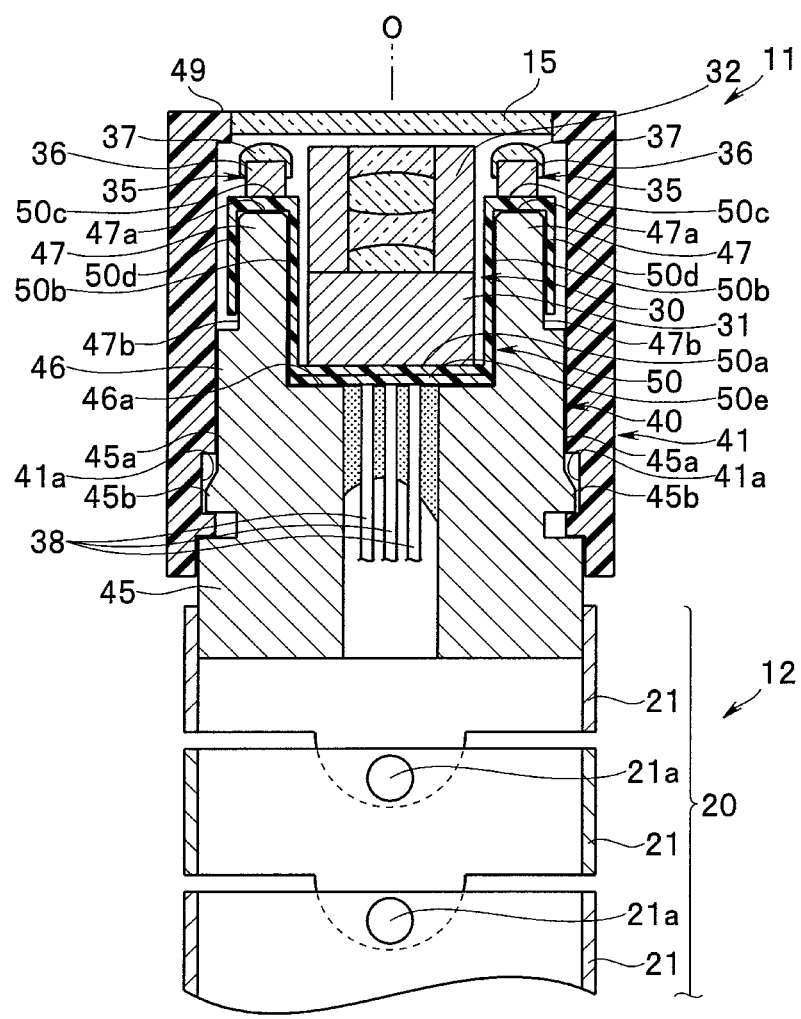
FIG. 10 relates to a second modification and is a sectional view of an essential part of a distal end portion.

As a combination of the light-receiving unit 30 and the light-emitting units 35, as illustrated in FIG. 10, for example, a combination of a light-receiving unit 30 in which an objective optical system 32 is disposed on a light-receiving surface side of an image pickup device 31 and light-emitting units 35 in which illumination optical systems 37 are respectively disposed on light-emission sides of light source elements 36 can be employed.

Figure 11:
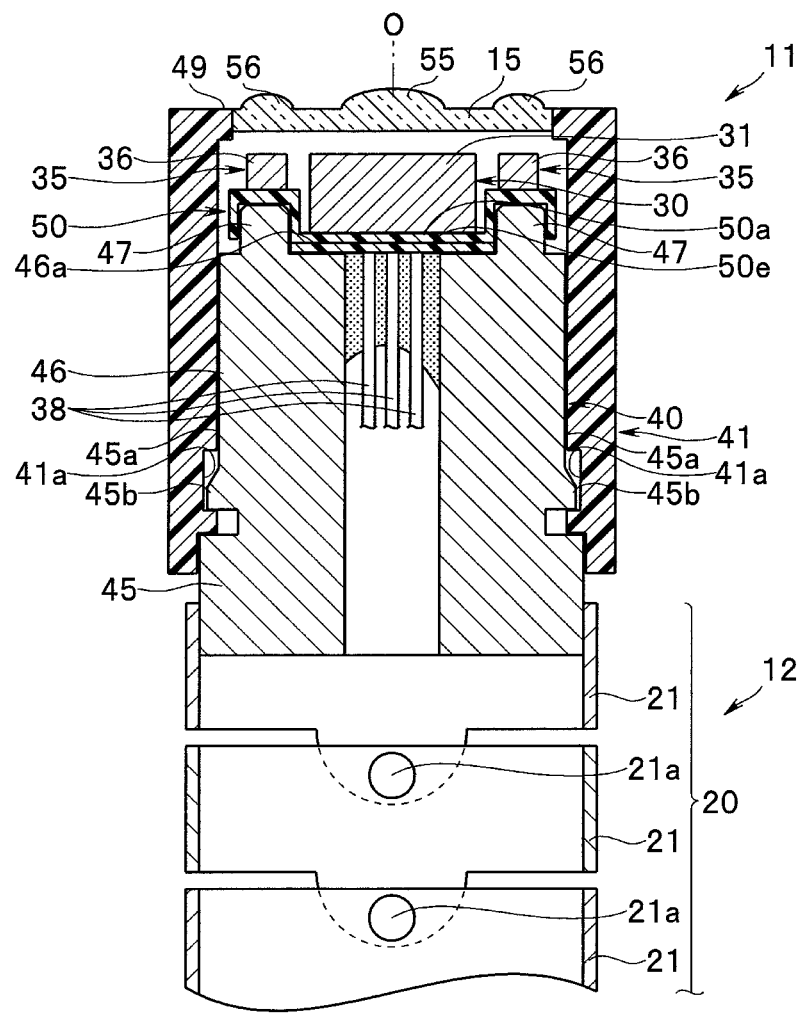
FIG. 11 relates to a third modification and is a sectional view of an essential part of a distal end portion.

In addition, as a combination of the light-receiving unit 30 and the light-emitting units 35, as illustrated in FIG. 11, for example, a combination of a light-receiving unit 30 configured by an image pickup device 31 as a single entity and light-emitting units 35 each configured by a light source element 36 as a single entity can be employed. In this case, an objective lens 55 opposed to the light-receiving unit 30 can be formed at a window portion 15. Furthermore, illumination optical systems 56 opposed respectively to the light-emitting units 35 can be appropriately provided at the window portion 15.

Figure 12:
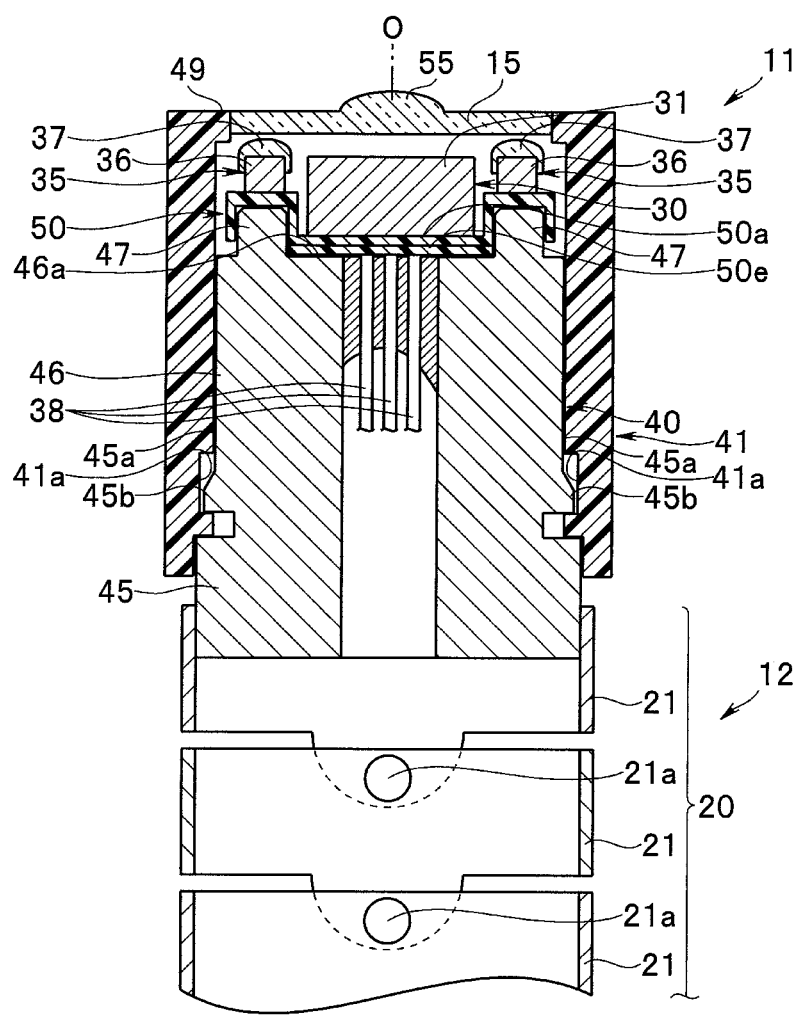
FIG. 12 relates to a fourth modification and is a sectional view of an essential part of a distal end portion.

Furthermore, as a combination of the light-receiving unit 30 and the light-emitting units 35, as illustrated in FIG. 12, for example, a combination of a light-receiving unit 30 configured by an image pickup device 31 as a single entity and light-emitting units 35 in which illumination optical systems 37 are disposed on the light-emission surface sides of light source elements 36 can be employed. In this case, an objective lens 55 opposed to the light-receiving unit 30 can be formed at a window portion 15.

Figure 13:
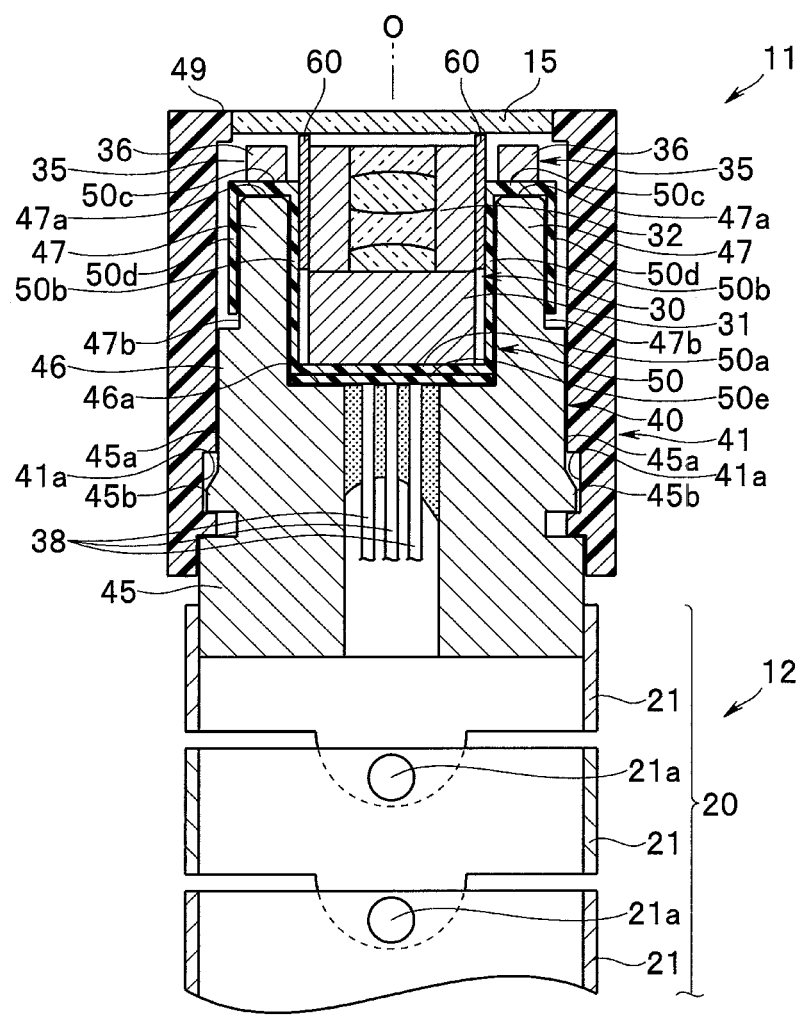
FIG. 13 relates to a fifth modification and is a sectional view of an essential part of a distal end portion.

In addition, as illustrated in FIG. 13, in order to prevent the light from each of the light-emitting units 35 from being directly incident on the light-receiving unit 30, light-shielding walls 60 can be provided between the light-receiving unit 30 and the respective light-emitting units 35.

Figure 14:
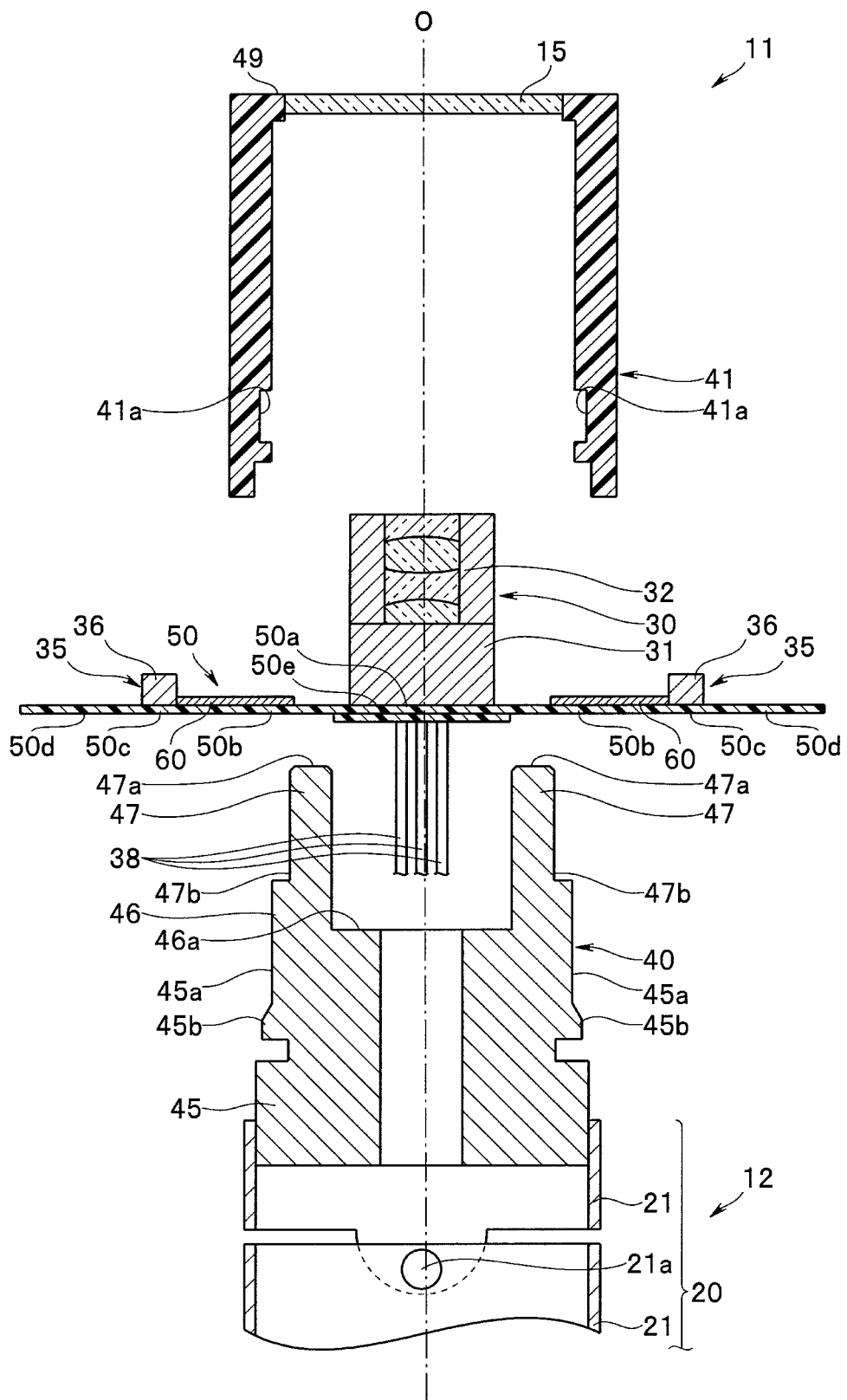
FIG. 14 relates to the fifth modification and is an explanatory view illustrating an assembly process of the distal end portion.
Figure 15:
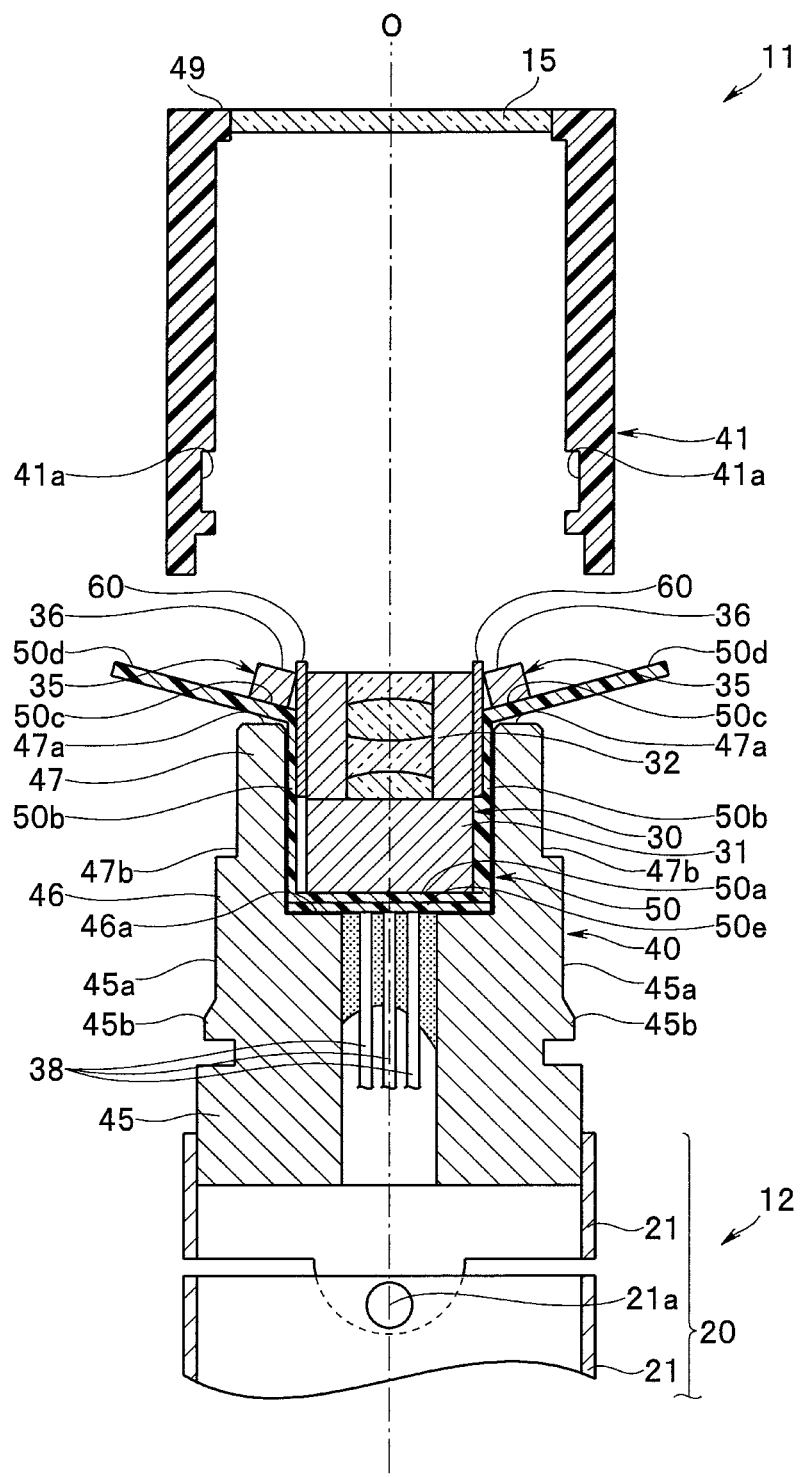
FIG. 15 relates to the fifth modification and is an explanatory view illustrating the assembly process of the distal end portion.
Figure 16:
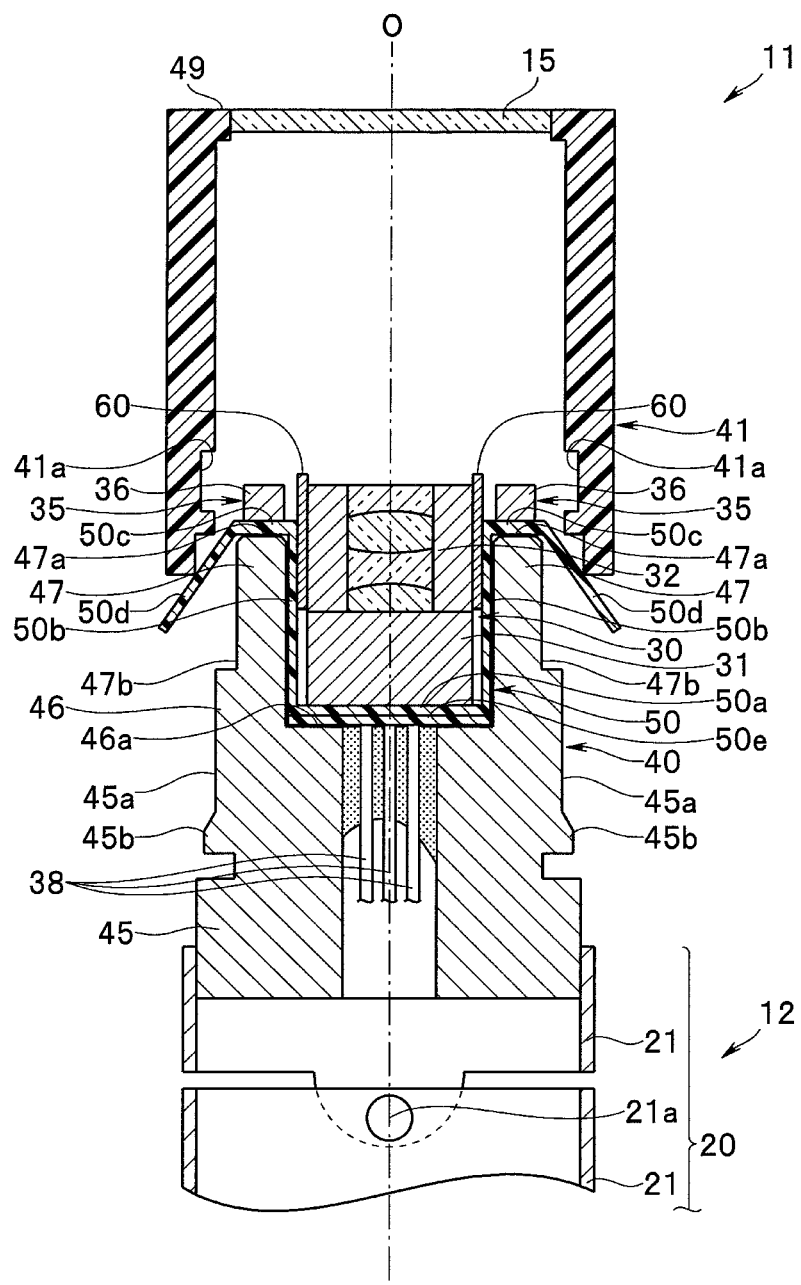
FIG. 16 relates to the fifth modification and is an explanatory view illustrating the assembly process of the distal end portion.

In this case, as illustrated in FIG. 14, for example, a part of each of the light-shielding walls 60 is adhered to each of the first extending sections 50b in advance (that is, the light-shielding walls 60 are mounted in advance on the FPC 50), to thereby enable each of the light-shielding walls 60 to be easily disposed between the light-receiving unit 30 and each of the light-emitting units 35 in the assembling process of the distal end portion 11 performed while bending the FPC 50 as illustrated in FIGS. 15 and 16.

Figure 17:
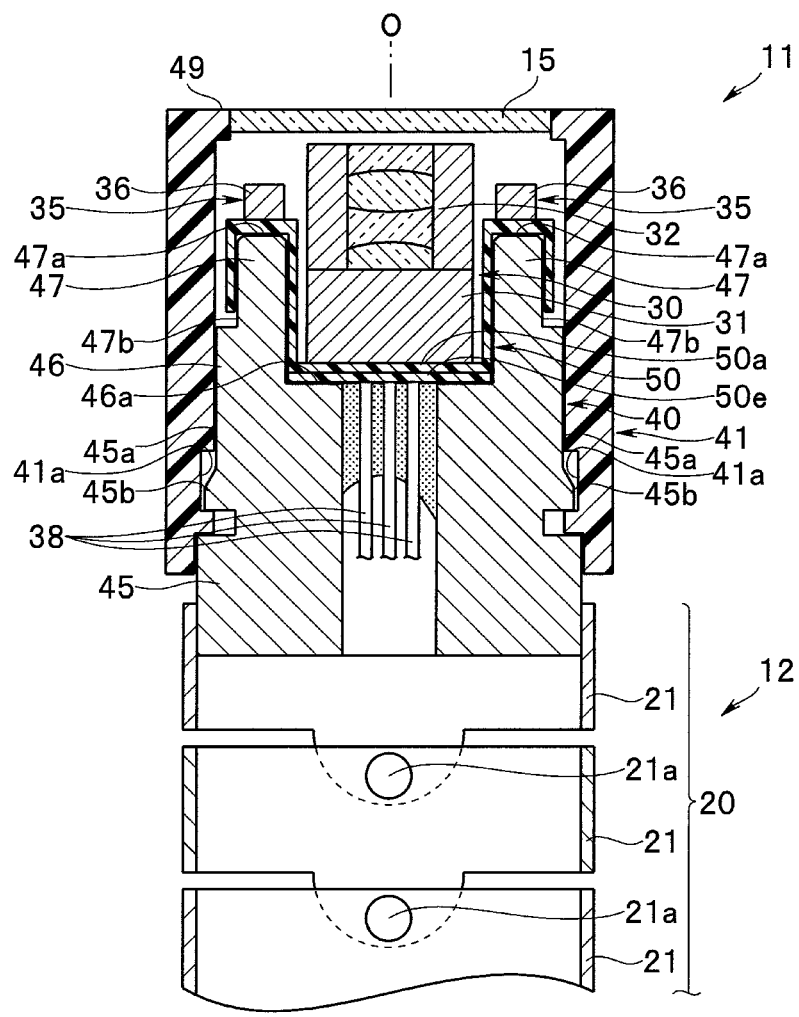
FIG. 17 relates to a sixth modification and is a sectional view of an essential part of a distal end portion.

In addition, in the above-described embodiment, as illustrated in FIG. 17, for example, the heights of the protruding portions 47 can be set such that the position of the distal end surface (the height viewed from the proximal end side of the distal end portion 11) of the light-receiving unit 30 in the direction of the optical axis O is located on the distal end side (so as to be higher) with respect to the positions of the respective distal end surfaces (the heights viewed from the proximal end side of the distal end portion 11) of the light-emitting units 35 in the direction of the optical axis O.

Figure 18:
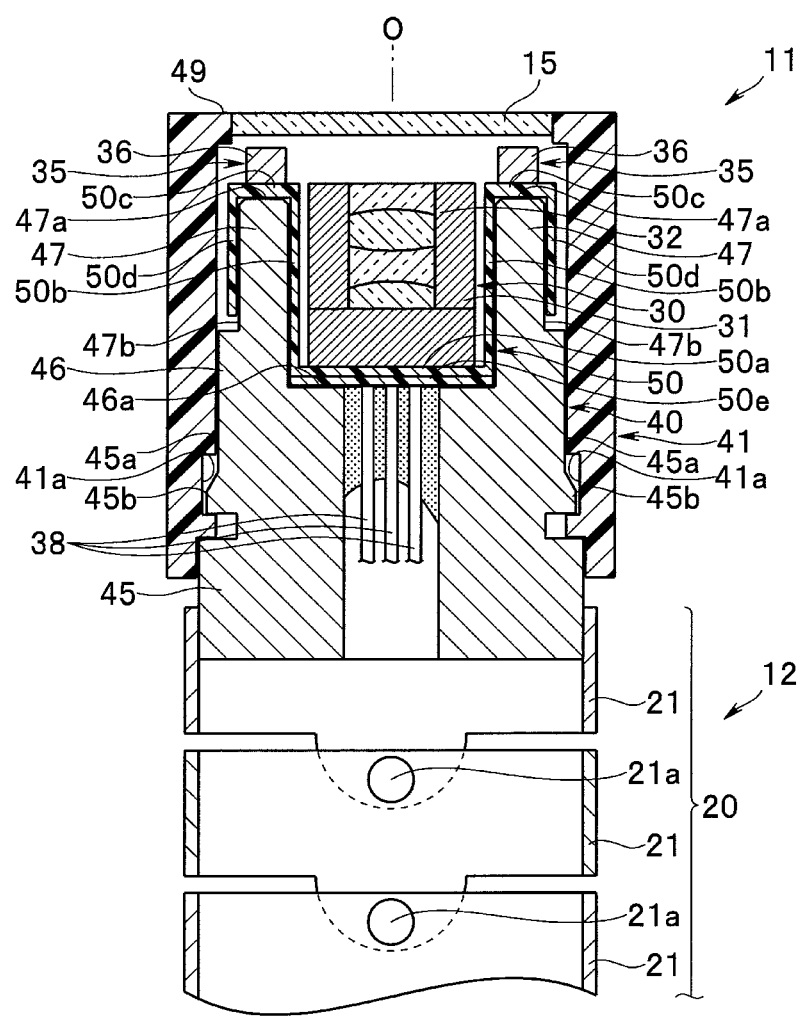
FIG. 18 relates to a seventh modification and is a sectional view of an essential part of a distal end portion.

Alternatively, as illustrated in FIG. 18, for example, the heights of the protruding portions 47 can be set such that the position of the distal end surface (the height viewed from the proximal end side of the distal end portion 11) of the light-receiving unit 30 in the direction of the optical axis O is located on the proximal end side (so as to be lower) with respect to the positions of the respective distal end surfaces (the heights viewed from the proximal end side of the distal end portion 11) of the light-emitting units 35 in the direction of the optical axis O.

Figure 19:
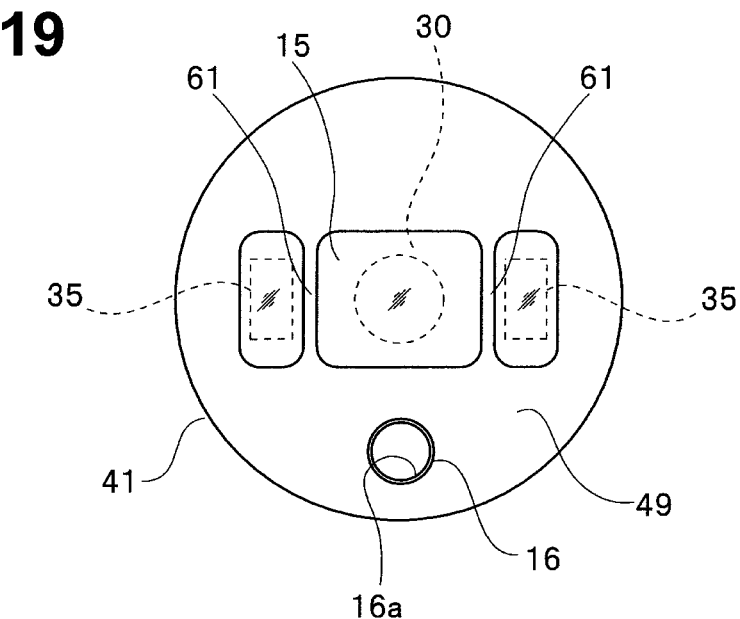
FIG. 19 relates to an eighth modification and is a view illustrating an end surface of a distal end portion.
Figure 20:
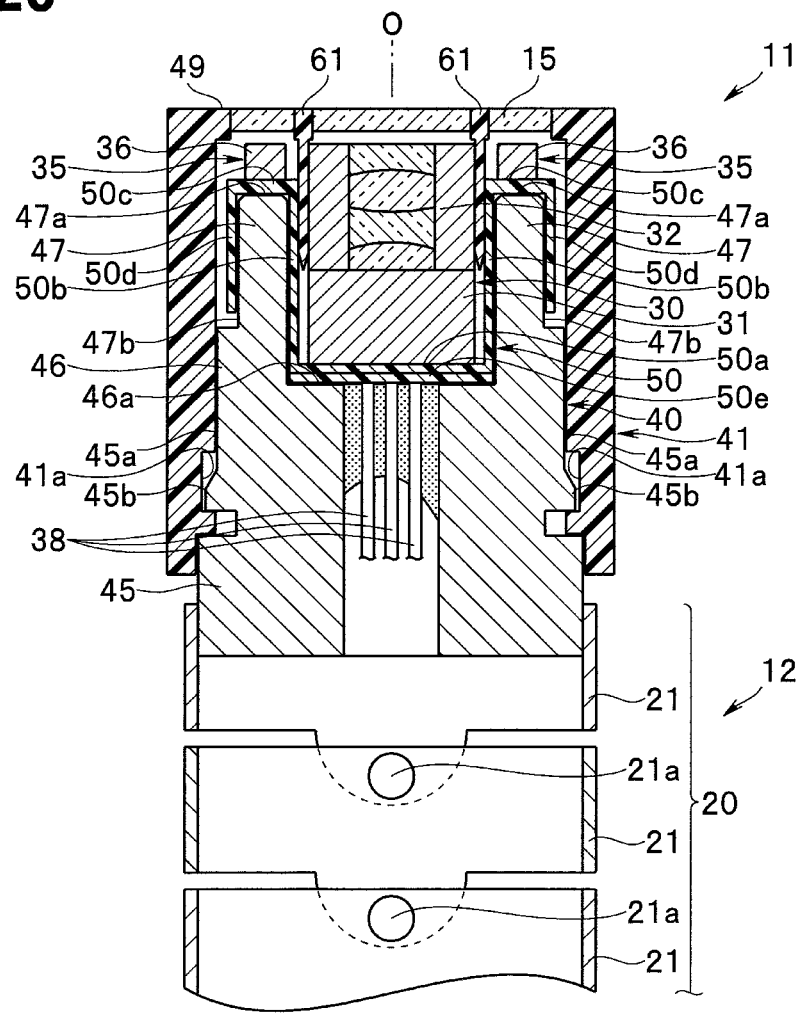
FIG. 20 relates to the eighth modification and is a sectional view of an essential part of the distal end portion.

Furthermore, in the above-described embodiment, as illustrated in FIGS. 19 and 20, for example, light-shielding walls 61 that protrude from the front wall portion 49 toward the inside of the distal end cover 41 can be provided, to thereby divide the window portion 15 into a region opposed to the light-receiving unit 30 and regions opposed to the respective light-emitting units 35.

Figure 21:
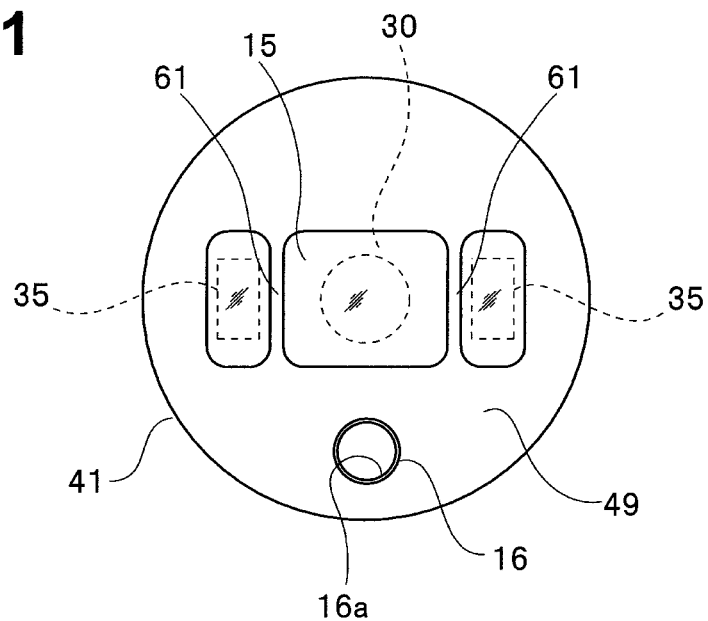
FIG. 21 relates to a ninth modification and is a view illustrating an end surface of a distal end portion.
Figure 22:
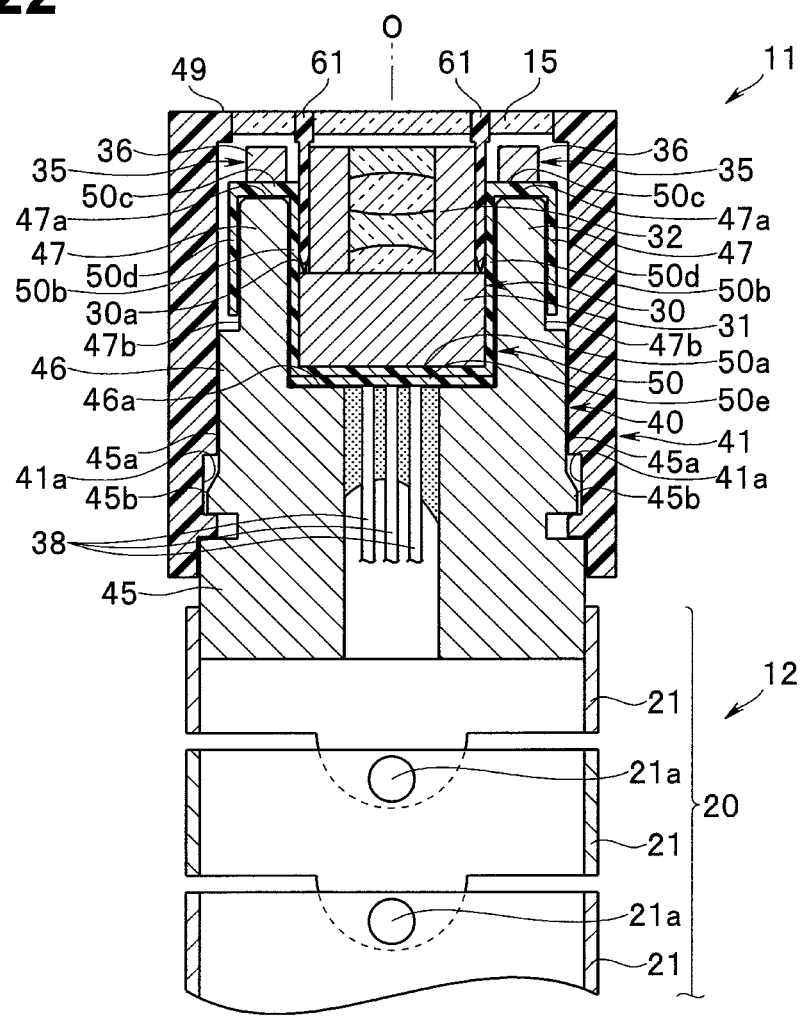
FIG. 22 relates to the ninth modification and is a sectional view of an essential part of the distal end portion.

Furthermore, as illustrated in FIGS. 21 and 22, for example, the light-shielding walls 61 that protrude from the front wall portion 49 into the distal end cover 41 are brought into contact with stepped portions 30a formed on the light-receiving unit 30, to cause the light-shielding walls 61 to press the light-receiving unit 30 against the first seat surface 46a, thereby be capable of fixing the light-receiving unit 30 to the stand 46 without using an adhesive or the like.

Note that the present invention is not limited to the above-described embodiment and each of the modifications, but various modifications and changes are possible, and such modifications and changes are also within the technical range of the present invention.

What is claimed is:

1. A distal end portion of an endoscope comprising:
   an image sensor having a first height;
   one or more light sources having a second height lower than the first height;
   a flexible printed circuit board on which an image sensor mounting section, a first extending section, a light source mounting section, and a second extending section are formed, the image sensor mounting section including a first surface on which the image sensor is mounted, the first extending section extending from the image sensor mounting section, the light source mounting section provided continuously to the first extending section and including a first surface on which the one or more light sources are mounted, and a second extending section extending from the light source mounting section;
   a stand including a seat surface on which a second surface of the image sensor mounting section is disposed in contact with the seat surface, the second surface being a rear surface of the first surface of the light source mounting section;
   a protruding portion protruded from the stand, with the protruding portion adjoining the seat surface, the protruding portion including an inner wall surface adjoining the seat surface, a protruding end surface, and an outer wall surface which is opposite side of the inner wall surface, wherein a second surface as a rear surface of the first extending section is disposed in contact with the inner wall surface, a second surface as a rear surface of the light source mounting section is disposed in contact with the protruding end surface, and a second surface as a rear surface of the second extending section is disposed in contact with the outer wall surface; and a cover that covers the image sensor, the one or more light sources, the stand, and the protruding portion.

2. The distal end portion of the endoscope according to claim 1, wherein the one or more light sources comprising a light-emitting diode, and a window provided on the cover is disposed so as to be opposed to the image sensor and the light-emitting diode.

3. The distal end portion of the endoscope according to claim 1, further comprising an objective lens provided on a distal end side of the image sensor, and the one or more light sources comprising a light-emitting diode.

4. The distal end portion of the endoscope according to claim 1, further comprising a light-shielding wall that shields between the image sensor and the one or more light sources.

5. The distal end portion of the endoscope according to claim 4, wherein the light-shielding wall is provided on the flexible printed circuit board.

6. The distal end portion of the endoscope according to claim 4, wherein the light-shielding wall is provided to the cover.

7. The distal end portion of the endoscope according to claim 6, wherein the light-shielding wall is configured to press the image sensor against the stand, in a state where the cover covers the stand and the protruding portion.

8. An endoscope insertion portion comprising the distal end portion of the endoscope according to claim 1.

9. An endoscope comprising the distal end portion of the endoscope according to claim 1.

\* \* \* \* \*